United States Patent
Kim et al.

(10) Patent No.: US 12,097,391 B2
(45) Date of Patent: Sep. 24, 2024

(54) ULTRASONIC GENERATOR WITH ADJUSTABLE ULTRASONIC FOCUSING DEPTH AND METHOD FOR TREATING OBESITY USING FOCAL DISTANCE CONTROL ACCORDING TO HORIZONTAL AND VERTICAL DIRECTIONS BY USING THE SAME

(71) Applicant: JEISYS MEDICAL INC., Seoul (KR)

(72) Inventors: Eun Ho Kim, Seoul (KR); Kyun Tae Kim, Seoul (KR); Kwang Hee Moon, Seoul (KR); Su Yong Lee, Seoul (KR); Min Young Kim, Seoul (KR); Won Ju Yi, Seoul (KR); Dong Hwan Kang, Seoul (KR)

(73) Assignee: Jeisys Medical Inc., Seoul (KR)

( * ) Notice: Subject to any disclaimer, the term of this patent is extended or adjusted under 35 U.S.C. 154(b) by 378 days.

(21) Appl. No.: 17/344,321

(22) Filed: Jun. 10, 2021

(65) Prior Publication Data

US 2021/0387023 A1 Dec. 16, 2021

(30) Foreign Application Priority Data

Jun. 11, 2020 (KR) .................. 10-2020-0071005
Jan. 7, 2021 (KR) .................. 10-2021-0001881

(51) Int. Cl.
*A61N 7/00* (2006.01)
*B06B 1/00* (2006.01)

(52) U.S. Cl.
CPC .................. *A61N 7/00* (2013.01); *B06B 1/00* (2013.01); *A61N 2007/0008* (2013.01)

(58) Field of Classification Search
CPC ............. A61N 7/00; A61N 2007/0008; A61N 2007/0082; A61N 2007/0091; A61N 7/02;

(Continued)

(56) References Cited

U.S. PATENT DOCUMENTS

2008/0021317 A1 1/2008 Sumanaweera
2012/0285251 A1* 11/2012 Rhim .................. A61N 7/02
73/632

(Continued)

FOREIGN PATENT DOCUMENTS

JP 2018-500075 A 1/2018
KR 10-2012-0040909 A 4/2012

(Continued)

OTHER PUBLICATIONS

The extended European search report issued by the European Patent Office on Nov. 16, 2021, which corresponds to European Patent Application No. 21177896.4-1113 and is related to U.S. Appl. No. 17/344,321.

(Continued)

*Primary Examiner* — Serkan Akar
*Assistant Examiner* — Gabriel Victor Popescu
(74) *Attorney, Agent, or Firm* — Leydig, Voit & Mayer, Ltd.

(57) ABSTRACT

Provided is an ultrasonic generator with an adjustable ultrasonic focusing depth. The ultrasonic generator with an adjustable ultrasonic focusing depth includes a cartridge housing in which an ultrasound generation portion generating ultrasonic waves is provided, a hand piece in which the cartridge housing is detachably mounted, the hand piece having a first actuator thereinside, and a main shaft to which the ultrasound generation portion is coupled so as to reciprocate in a horizontal direction, parallel to the bottom of the cartridge housing and a vertical direction, perpendicular to the bottom of the cartridge housing. One end of the main shaft is coupled to one end of the first actuator of the hand piece, and an other end of the main shaft is located inside the cartridge housing. The hand piece includes an adjustment (Continued)

portion adjusting an ultrasonic focusing depth of the ultrasound generation portion.

12 Claims, 13 Drawing Sheets

(58) Field of Classification Search
CPC .... A61N 2007/0056; A61N 2007/0065; B06B 1/00
See application file for complete search history.

(56) References Cited

U.S. PATENT DOCUMENTS

| | | | |
|---|---|---|---|
| 2014/0081301 A1* | 3/2014 | Tran | A61N 2007/0091 606/169 |
| 2016/0243382 A1 | 8/2016 | Jo | |
| 2019/0366129 A1* | 12/2019 | Park | A61N 7/00 |
| 2020/0100762 A1* | 4/2020 | Barthe | A61N 7/00 |

FOREIGN PATENT DOCUMENTS

| | | | | |
|---|---|---|---|---|
| KR | 10-1226659 B1 | 2/2013 | | |
| KR | 10-1335476 B1 | 12/2013 | | |
| KR | 10-1429002 B1 | 8/2014 | | |
| KR | 10-1487497 B1 | 1/2015 | | |
| KR | 10-2016-0063119 A | 6/2016 | | |
| KR | 10-1677903 B1 | 11/2016 | | |
| KR | 10-1700334 B1 | 1/2017 | | |
| KR | 10-2017-0015269 A | 2/2017 | | |
| KR | 10-2018-0015095 A | 2/2018 | | |
| KR | 10-2019-0009209 A | 1/2019 | | |
| KR | 10-2020-0006861 A | 1/2020 | | |
| KR | 10-2078651 B1 | 2/2020 | | |
| KR | 102118017 B1 * | 6/2020 | | A61N 7/02 |
| WO | 2014/081062 A1 | 5/2014 | | |

OTHER PUBLICATIONS

The extended European search report issued by the European Patent Office on Jan. 18, 2023, which corresponds to European Patent Application No. 22201785.7-1113 and is related to U.S. Appl. No. 17/344,321.

An Office Action; "Notice of Reasons for Refusal," mailed by the Japanese Patent Office on Jun. 14, 2022, which corresponds to Japanese Patent Application No. 2021-096566 and is related to U.S. Appl. No. 17/344,321.

A Notice of Allowance mailed by the Korean Intellectual Property Office on Mar. 30, 2021, which corresponds to Korean Patent Application No. 10-2021-0001881 and is related to U.S. Appl. No. 17/344,321.

* cited by examiner

ULTRASONIC GENERATOR WITH ADJUSTABLE ULTRASONIC FOCUSING DEPTH AND METHOD FOR TREATING OBESITY USING FOCAL DISTANCE CONTROL ACCORDING TO HORIZONTAL AND VERTICAL DIRECTIONS BY USING THE SAME

CROSS-REFERENCE TO RELATED APPLICATIONS

A claim for priority under 35 U.S.C. § 119 is made to Korean Patent Application No. 10-2020-0071005 filed on Jun. 11, 2020 and Korean Patent Application No. 10-2021-0001881 filed on Jan. 7, 2021 in the Korean Intellectual Property Office, the entire contents of which are hereby incorporated by reference.

Technical Field

Embodiments of the inventive concept described herein relate to an ultrasonic generator with an adjustable ultrasonic focusing depth including a hand piece and a cartridge housing that is detachably coupled to the hand piece and generating ultrasonic waves.

Background Art

In recent years, various diet programs and ultrasonic obesity treatment apparatuses for the treatment of obesity have been developed and widely used.

In particular, high intensity focused ultrasound (HIFU) obesity treatment technology has been used for cancer treatment that destroys cancer cells by non-invasively and selectively coagulating an internal organ tumor at high temperature. For the purpose of the treatment of abdominal obesity in the human body, Solta Medical, Inc. in the USA first developed equipment, called Liposonix, which has HIFU mounted therein.

A process of destroying fat using HIFU is a process of destroying tissue by instantaneously raising the temperature of the tissue to 65° C. to 100° C. by focusing HIFU on a predetermined point of a fat cell.

Unlike other dermatological equipment such as a laser and RF equipment, HIFU equipment induces coagulation necrosis of fat cells by non-invasively focusing HIFU energy on a selected portion without causing damage to the skin surface. The necrotized fat cells are naturally removed by a damaged portioncell recovery mechanism of the human body.

Meanwhile, ultrasonic obesity treatment apparatuses include a head or hand piece for breaking down subcutaneous fat of a patient by generating HIFU under the control of a controller.

Various ultrasonic generators for ultrasonic obesity treatment are provided, depending on ultrasonic focusing depths. To improve convenience of treatment by minimizing the inconvenience of needing to replace a cartridge, technologies for moving an ultrasonic focusing depth of a transducer have been proposed.

However, a complicated configuration such as a configuration for solving a problem of heat generated by a flow of a ultrasound transmission medium (for example, liquid) filled in a cartridge according to repeated movements of a transducer installed in the cartridge, a configuration for smoothly guiding the liquid flow, or the like, is required.

DETAILED DESCRIPTION OF THE INVENTION

Technical Problem

Embodiments of the inventive concept provide an ultrasonic generator having a function of altering an ultrasonic focusing depth.

The problems to be solved by the inventive concept are not limited to the aforementioned problems, and any other problems not mentioned herein will be clearly understood from the following description by those skilled in the art to which the inventive concept pertains.

Technical Solution

According to an embodiment, an ultrasonic generator with an adjustable ultrasonic focusing depth includes a cartridge housing in which an ultrasound generation portion generating ultrasonic waves is provided, a hand piece in which the cartridge housing is detachably mounted, the hand piece having a first actuator thereinside, and a main shaft to which the ultrasound generation portion is coupled so as to reciprocate in a horizontal direction, parallel to the bottom of the cartridge housing and a vertical direction, perpendicular to the bottom of the cartridge housing. One end of the main shaft is coupled to one end of the first actuator of the hand piece, and an other end of the main shaft is located inside the cartridge housing. The hand piece may further include an adjustment portion adjusting an ultrasonic focusing depth of the ultrasound generation portion by adjusting an amount of movement of the main shaft in the vertical direction.

The ultrasonic generator may further include an auxiliary shaft that is accommodated in the cartridge housing, disposed parallel to the main shaft and guiding a movement of the ultrasound generation portion in the vertical direction and the horizontal direction.

The ultrasonic generator may further include a movable plate to which the main shaft is fixed, the movable plate being provided so as to be movable inside the hand piece in the vertical direction.

The adjustment portion may be located to press one side surface of the movable plate for reciprocation of the ultrasound generation portion in the vertical direction, and the ultrasonic generator may further include a first elastic member that is disposed on an opposite side to the adjustment portion in the vertical direction with the movable plate therebetween and that elastically supports an opposite side surface of the movable plate.

The ultrasonic generator may further include second elastic members that are provided at both ends of the auxiliary shaft in a lengthwise direction and that elastically support a movement of the main shaft in the vertical direction and a guide member that slides along an outer circumferential surface of the auxiliary shaft. The ultrasound generation portion may be fixed to a lower mount protruding from the guide member to one side, and an upper mount protruding from the guide member to an other side may be coupled to surround an outer circumferential surface of the main shaft.

The main shaft may include a screw shaft that is directly connected to the first actuator and that integrally rotates together with the first actuator, a screw nut that is screw-coupled to a thread formed on an outer circumferential surface of the screw shaft and that moves in the horizontal direction when the screw shaft rotates, a length adjustment rod that is integrally coupled to the screw nut and that moves together with the screw nut, and an insert protrusion formed on an end portion of the length adjustment rod exposed from the hand piece, the insert protrusion being detachably coupled to the upper mount.

The upper mount may include an insert recess into which the insert protrusion is inserted, and a first tube and a second tube may be disposed at both ends of the insert recess in the horizontal direction.

The insert protrusion may include a magnetic member having a polarity, and the insert recess may include a magnetic member having a polarity opposite to the polarity of the magnetic member of the insert protrusion.

An inclined guide surface having an inner diameter greater than a diameter of the insert protrusion may be formed at an inlet side of the insert recess, and the inner diameter of the inclined guide surface may be gradually decreased and may be formed to converge to the diameter of the insert protrusion.

The first tube may be spaced apart from an outer circumferential surface of the length adjustment rod so as to surround the length adjustment rod and may have one end supported on an inside wall of the cartridge housing in the horizontal direction and an other end pressed against the upper mount.

The second tube may be coaxially disposed to face the first tube with the upper mount therebetween and may have one end pressed against the upper mount and an other end supported on an inside wall of the cartridge housing.

The upper mount may further include a fixing member formed such that portions of outer circumferential surfaces of the first and second tubes are simultaneously stopped by and fixed to the fixing member between the first tube and the second tube.

The ultrasonic generator may further include a second actuator that moves the movable plate in the vertical direction. A screw shaft may be coupled to the second actuator, and a screw nut screw-coupled to the screw shaft may be provided on the movable plate.

According to an embodiment, there is provided a method for treating obesity by moving distance control according to horizontal and vertical directions using an ultrasonic generator including a cartridge housing in which an ultrasound generation portion generating ultrasonic waves is provided, a hand piece in which the cartridge housing is detachably mounted, the hand piece having a first actuator thereinside, and a main shaft to which the ultrasound generation portion is coupled so as to reciprocate in a horizontal direction, parallel to the bottom of the cartridge housing and a vertical direction, perpendicular to the bottom of the cartridge housing, the main shaft having one end coupled to one end of the first actuator of the hand piece and an opposite end located inside the cartridge housing.

In addition, the ultrasound generation portion may move within a range of 0.1 mm to 30 mm in the horizontal direction and within a range of 0.1 mm to 5 mm in the vertical direction.

In addition, the movement in the horizontal direction and the movement in the vertical direction may be alternately performed.

Other specific details of the inventive concept are included in the detailed description and the drawings.

Advantageous Effects of the Invention

According to the ultrasonic generator with the adjustable ultrasonic focusing depth according to an embodiment of the inventive concept, it is possible to minimize the inconvenience of needing to purchase cartridges having corresponding ultrasonic focusing depths, or replace a provided cartridge, depending on various fat layer thicknesses or abdominal circumferences of persons undergo procedures.

Effects of the inventive concept are not limited to the aforementioned effects, and any other effects not mentioned herein will be clearly understood from the following description by those skilled in the art to which the inventive concept pertains.

BEST MODE

Figure 1:
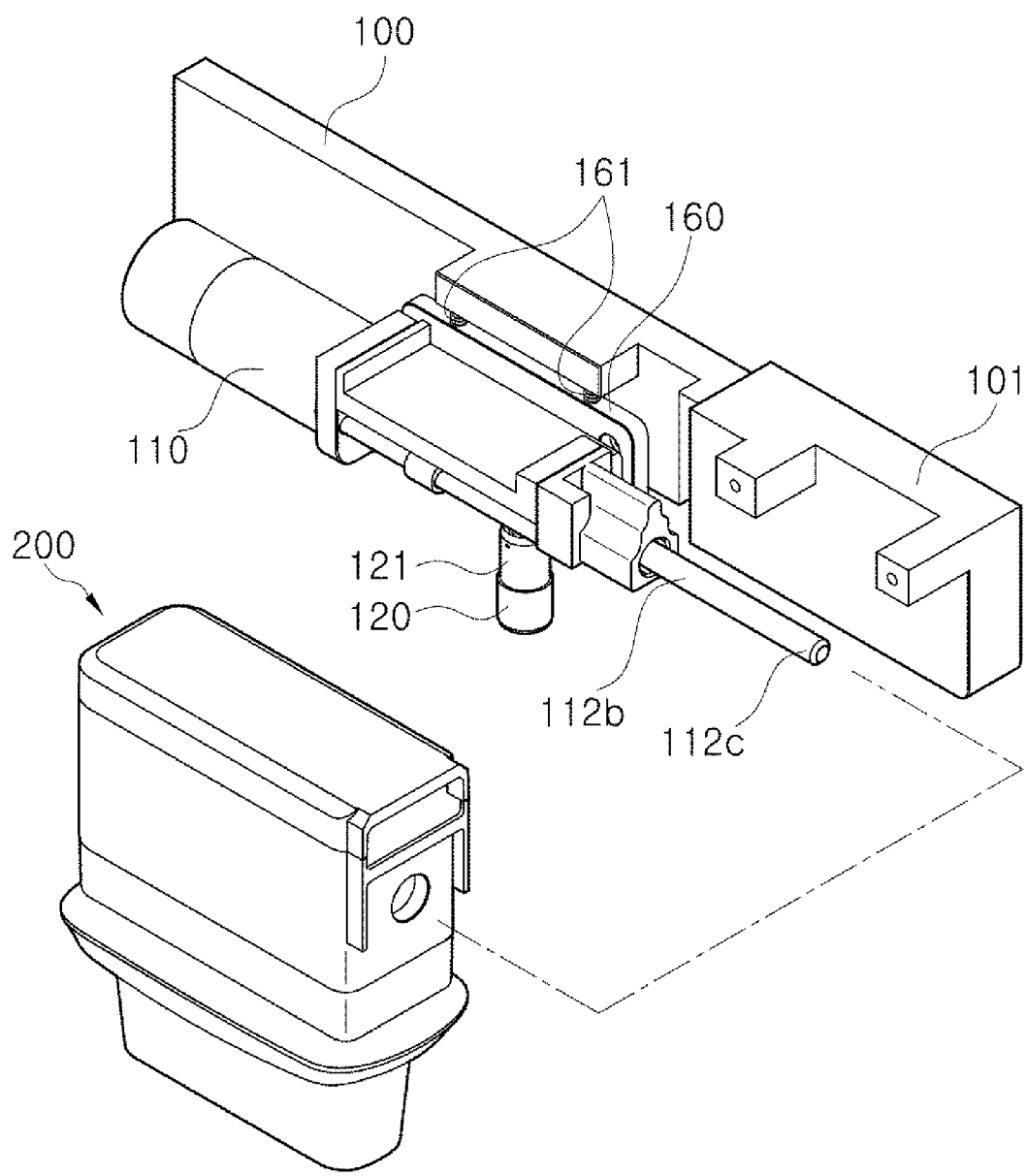
FIG. 1 is a perspective view illustrating a state in which a cartridge housing of an ultrasonic generator with an adjustable ultrasonic focusing depth according to an embodiment of the inventive concept is separated.

The above and other aspects, features, and advantages of the inventive concept will become apparent from the following description of embodiments given in conjunction with the accompanying drawings. However, the inventive concept is not limited to the embodiments disclosed herein and may be implemented in various different forms. Herein, the embodiments are provided to provide complete disclosure of the inventive concept and to provide thorough understanding of the inventive concept to those skilled in the art to which the inventive concept pertains, and the scope of the inventive concept should be limited only by the accompanying claims and equivalents thereof.

Terms used herein are only for description of embodiments and are not intended to limit the inventive concept. As used herein, the singular forms are intended to include the plural forms as well, unless context clearly indicates otherwise. It will be further understood that the terms "comprise" and/or "comprising" specify the presence of stated features, components, and/or operations, but do not preclude the presence or addition of one or more other features, components, and/or operations. In addition, identical numerals will denote identical components throughout the specification, and the meaning of "and/or" includes each mentioned item and every combination of mentioned items. It will be understood that, although the terms first, second, etc. may be used herein to describe various components, these components should not be limited by these terms. These terms are only used to distinguish one component from another component. Thus, a first component discussed below could be termed a second component without departing from the teachings of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should not be interpreted in an idealized or overly formal sense unless expressly so defined herein.

Spatially relative terms, such as "beneath", "below", "lower", "above", "upper" and the like, may be used herein for ease of description to describe one component or feature's relationship to another component(s) or feature(s) as illustrated in the figures. It will be understood that the spatially relative terms are intended to encompass different orientations of the device in use or operation in addition to the orientation depicted in the figures. For example, if the component in the figures is turned over, components described as "below" or "beneath" other components or features would then be oriented "above" the other components or features. Thus, the exemplary term "below" can encompass both an orientation of above and below. The component may be otherwise oriented and the spatially relative descriptors used herein interpreted accordingly.

Hereinafter, the inventive concept will be described in detail with reference to the accompanying drawings.

Figure 2:
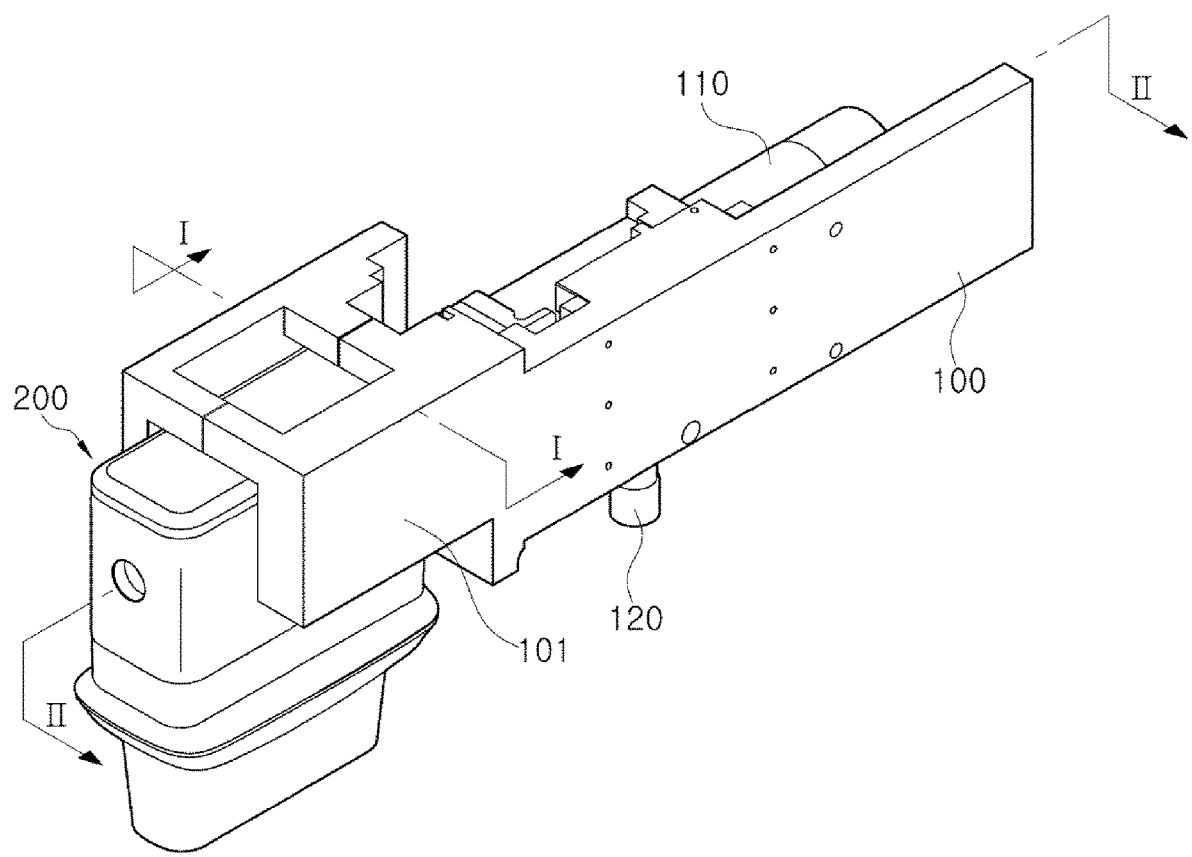
FIG. 2 is a perspective view illustrating a coupled state of FIG. 1.
Figure 3:
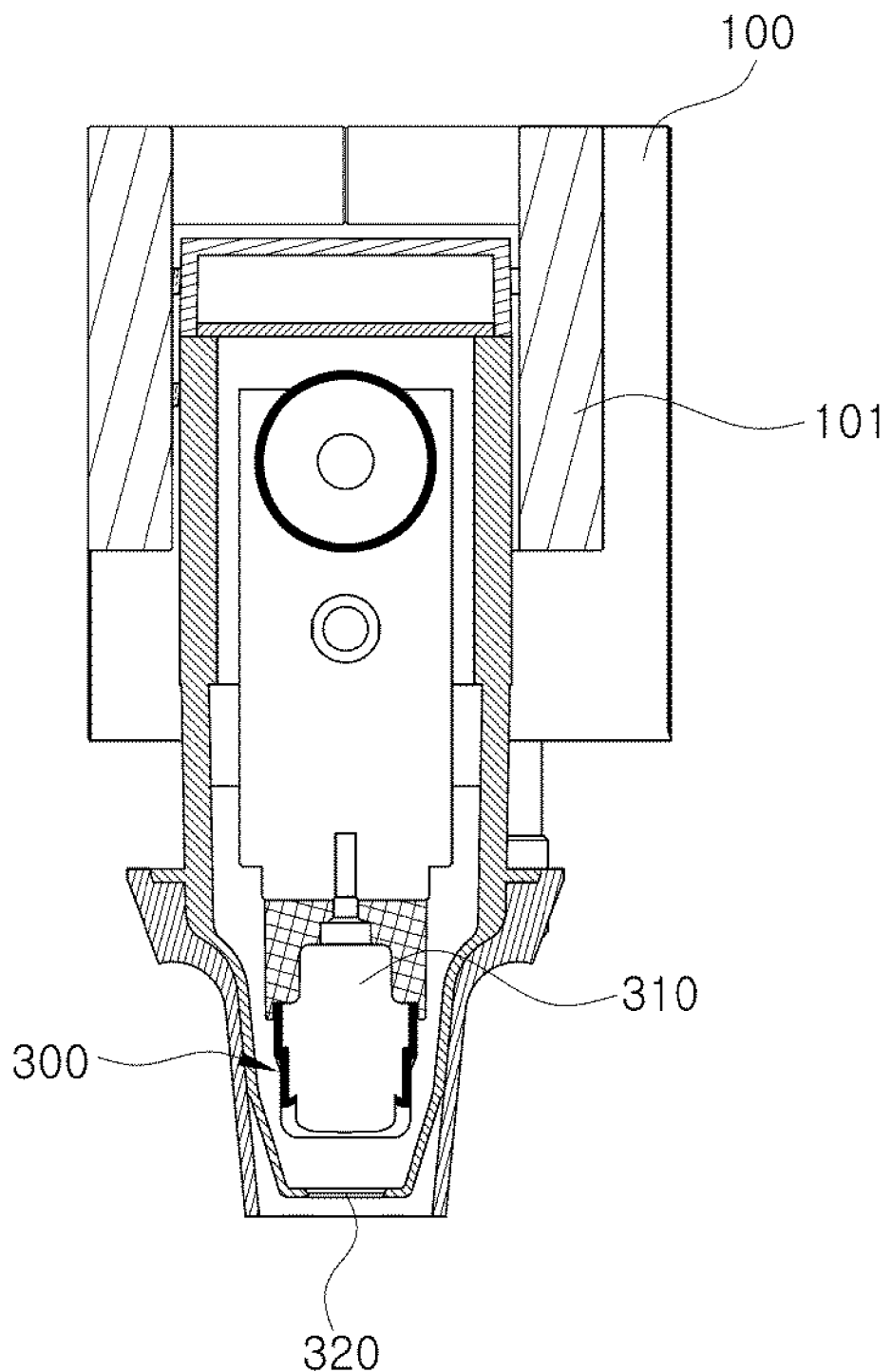
FIG. 3 is a sectional view taken along line I-I of FIG. 2.
Figure 4:
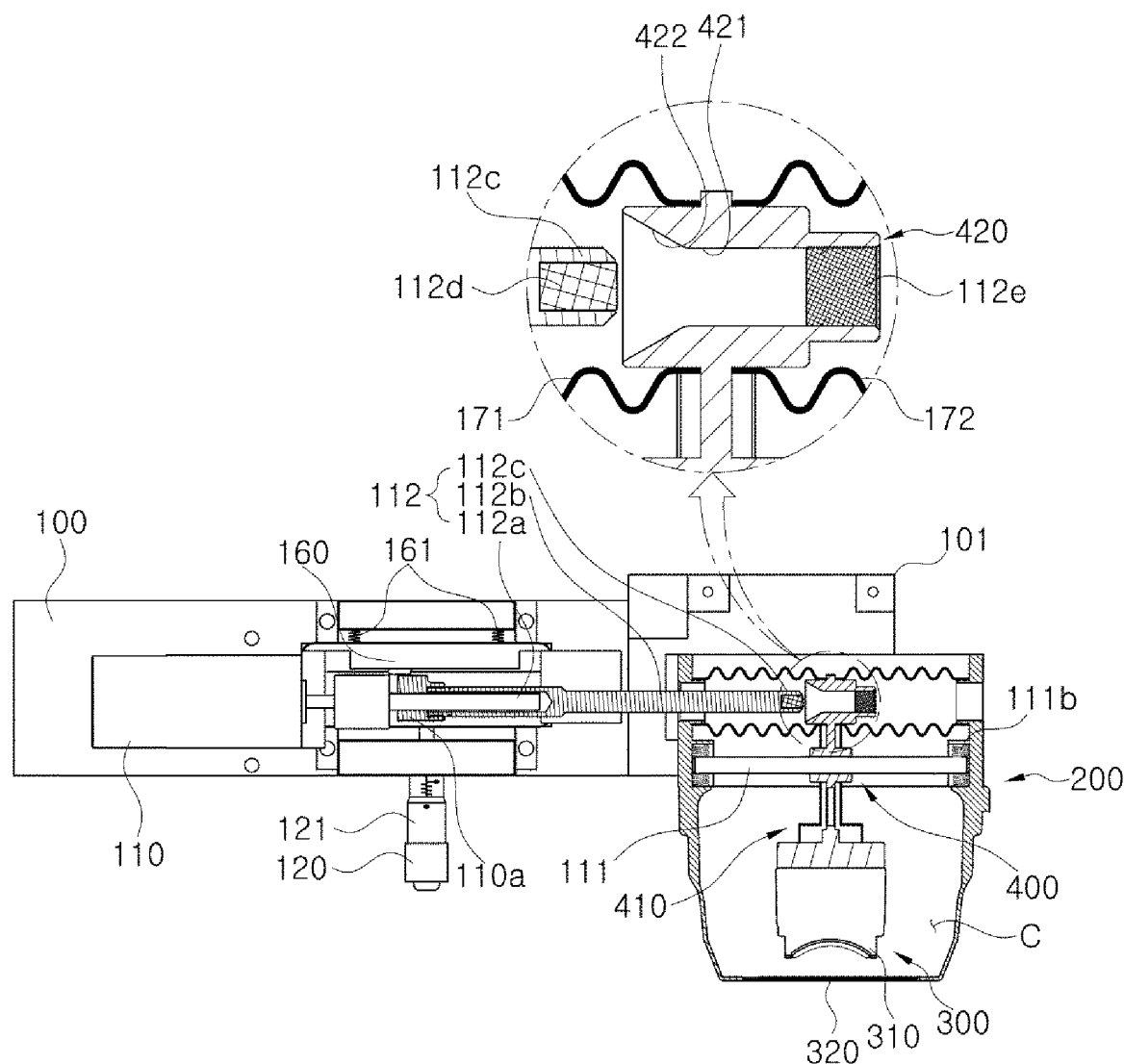
FIG. 4 is a sectional view taken along line II-II of FIG. 2.
Figure 5:
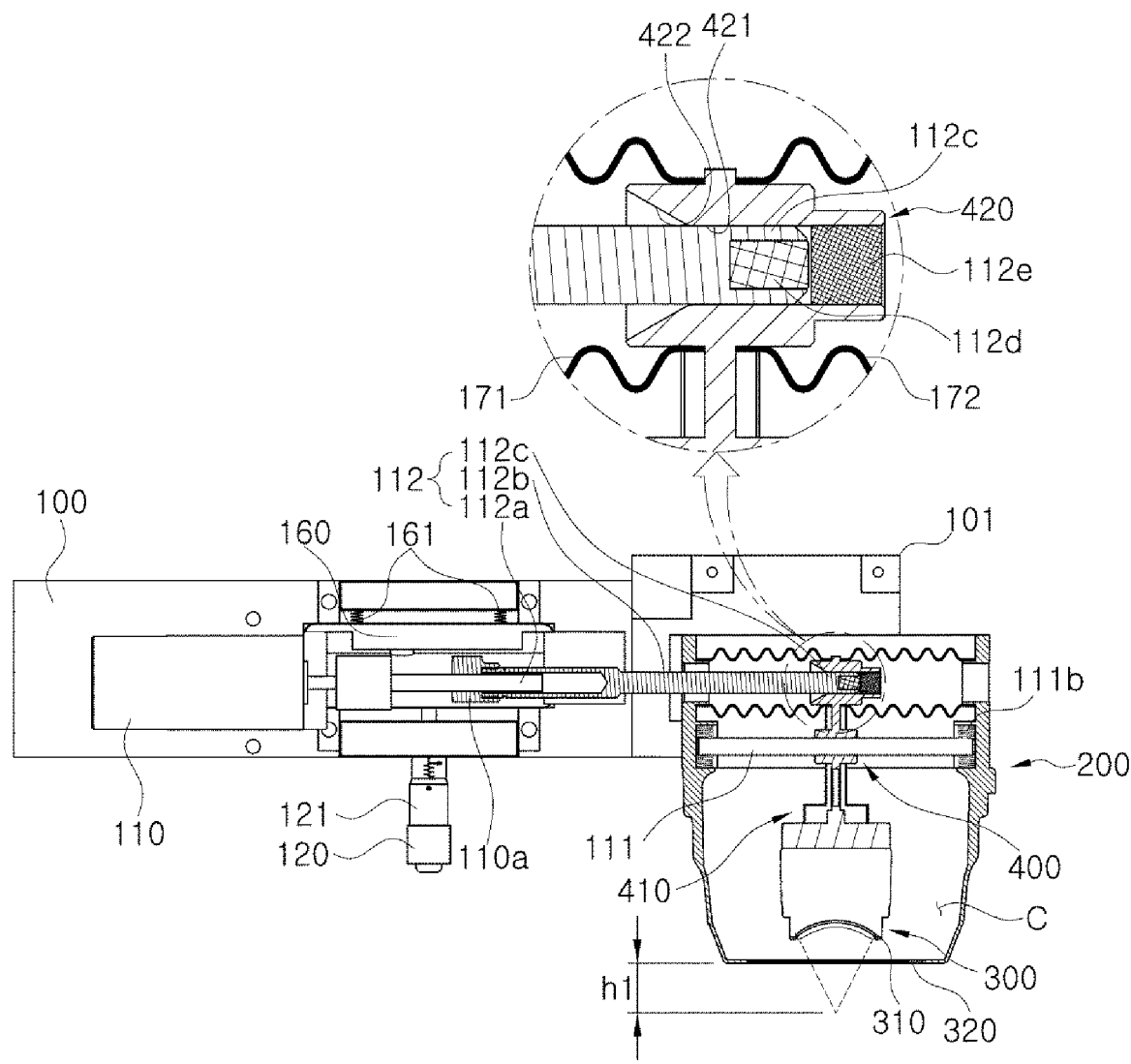
FIG. 5 is a sectional view illustrating a state in which an insert protrusion of FIG. 4 is inserted into an insert recess.

FIG. 1 is a perspective view illustrating a state in which a cartridge housing of an ultrasonic generator with an adjustable ultrasonic focusing depth according to an embodiment of the inventive concept is separated. Specifically, FIG. 1 is a perspective view in which one side surface of the cartridge housing 200 is illustrated to be visible. In addition, FIG. 2 is a perspective view illustrating a coupled state of FIG. 1. FIG. 3 is a sectional view taken along line I-I of FIG. 2. FIG. 4 is a sectional view taken along line II-II of FIG. 2. FIG. 5 is a sectional view illustrating a state in which an insert protrusion of FIG. 4 is inserted into an insert recess.

As illustrated in FIGS. 1 to 4, the ultrasonic generator with the adjustable ultrasonic focusing depth according to an embodiment of the inventive concept may include a hand piece 100 and 101, the cartridge housing 200, an auxiliary shaft 111, a main shaft 112, an adjustment portion 120 and 121, and an ultrasound generation portion 300.

Referring to the accompanying drawings related to this embodiment, a configuration of a case (not illustrated) that forms the exterior of the hand piece 100 and 101 is not illustrated, and for convenience of description, the base frame 100 and the mounting frame 101 provided inside the case are collectively referred to as the hand piece 100 and 101.

The case may form the exterior of the hand piece 100 and 101 and may have a shape that an operator can grasp with a hand. The case may be formed in various shapes considering ergonomic design.

The operator may perform a procedure by a method of emitting focused ultrasound in a state in which the operator holds a portion of the case with a hand and adjusts the position of the cartridge housing 120 such that the cartridge housing 200 is brought into contact with a portion to be treated. The case may include, on an outer surface thereof, a handle (not illustrated) that has a non-slip function for prevention of a slip when the operator grasps the case.

Inside the cartridge housing 200, the ultrasound generation portion 300 generating ultrasonic waves may be provided.

Furthermore, inside the cartridge housing 200, the auxiliary shaft 111 to which the ultrasound generation portion 300 is coupled is accommodated to reciprocate in a horizontal direction.

Hereinafter, a vertical direction and a horizontal direction are not limited to a geometrical vertical direction and a geometrical horizontal direction, and may refer to an up/down direction and a left/right direction, respectively, in the accompanying drawings. Although the horizontal direction and the vertical direction are defined as directions perpendicular to each other, the vertical direction is not defined as the geometrical vertical direction in the strict sense. In other words, a direction closer to the vertical direction rather than the horizontal direction has to be understood as being vertical.

The main shaft 112 may be disposed above the auxiliary shaft 111 so as to be parallel to the auxiliary shaft 111. The main shaft 112 is connected to the ultrasound generation portion 300 through a guide member 400 that will be described below. Accordingly, as the main shaft 112 moves in the vertical direction and the horizontal direction, the ultrasound generation portion 300 may also move in the vertical direction and the horizontal direction in conjunction with the movement of the main shaft 112. Here, the main shaft 112 may be disposed below the auxiliary shaft 111 so as to be parallel to the auxiliary shaft 111. However, the inventive concept is not particularly limited thereto.

The cartridge housing 200 may be detachably mounted in the hand piece 100 and 101. A first actuator 110 provided on the hand piece 100 and 101 may be coupled to one end of the main shaft 112, and an other end of the main shaft 112 may be located inside the cartridge housing 200.

The hand piece 100 and 101 may include the base frame 100 and the mounting frame 101 that is located on the opposite side to the base frame 100 and in which the cartridge housing 200 is mounted.

The first actuator 110 may be provided on the base frame 100 as described above. A forward/reverse motor, a hydraulic motor, a pneumatic motor, an engine, or the like that can rotate in a forward or reverse direction and can generate rotary power may be used as the first actuator 110. However, the first actuator 110 is not limited thereto, and any types of devices capable of supplying rotating torque to the main shaft 112 may be used as the first actuator 110.

The main shaft 112 may be directly connected to the first actuator 110 at the one end thereof to receive rotary power from the first actuator 110 and may be coupled to the cartridge housing 200 such that the other end of the main shaft 112 is located inside the cartridge housing 200. The mounting frame 101 may be formed to have a space in which the cartridge housing 200 is detachably mounted. The space may refer to an inner space formed in a thickness direction of the mounting frame 101.

Referring to FIGS. 2 to 5, the adjustment portion 120 and 121 adjusts a movement of the main shaft 112 in the vertical direction to adjust the ultrasonic focusing depth of the ultrasound generation portion 300 that will be described below. Here, the main shaft 112 is fixed to a movable plate 160 provided to be movable inside the hand piece 100 and 101 in the vertical direction. The main shaft 112 may be moved in the vertical direction by the adjustment portion 120 and 121, and a description thereabout will be given below.

When the main shaft 112 is moved in the vertical direction by the adjustment portion 120 and 121, the first actuator 110, the auxiliary shaft 111 to be described below, the movable plate 160, a transducer 310, and the guide member 400 may also be moved together in the vertical direction, and thus the ultrasonic focusing depth of the ultrasound generation portion 300 may be adjusted. A description thereabout may also be given below.

For example, the adjustment portion 120 and 121 may be, but is not limited to, a rotary adjustment portion that adjusts a vertical movement through rotation or a button type adjustment portion that adjusts a vertical movement through linear movement.

In a case where the adjustment portion 120 and 121 is a rotary adjustment portion, the adjustment portion 120 and 121 may include the outer rotor 120 that a user grasps and rotates and the inner rotor 121 having one portion that is located inside the outer rotor 120 in the radial direction and another portion that protrudes from the outer rotor 120 toward the movable plate 160 depending on rotation of the outer rotor 120 to adjust the length thereof.

The outer rotor 120 and the inner rotor 121 may be disposed on the same axis. One of the outer rotor 120 and the inner rotor 121 may be rotated, and the other may be rotated in a screw-coupled state to adjust the length by which the other protrudes toward the movable plate 160.

Although the height adjustment structure using the adjustment portion 120 and 121 is described as an example in this embodiment, the adjustment portion 120 and 121 is not limited to the structure of the outer rotor 120 and the inner rotor 121 screw-coupled to each other, and any structure, such as a rack and pinion or a ratchet structure, which can adjust length may be applied to the adjustment portion 120 and 121.

In addition, graduations may be marked on an outer circumferential surface of the outer rotor 120 or the inner rotor 121 such that the user recognizes the distance by which the movable plate 160 moves in the vertical direction.

First elastic members 161 may be disposed on the opposite side to the adjustment portion 120 and 121 with the movable plate 160 therebetween.

The first elastic members 161 elastically support the movable plate 160 pressed by the adjustment portion 120 and 121. The movable plate 160 moves upward when the adjustment portion 120 and 121 is rotated in the forward direction and moves downward when the adjustment portion 120 and 121 is rotated in the reverse direction.

The main shaft 112 may include a screw shaft 112a directly connected to the first actuator 110 to rotate, a length adjustment rod 112b screw-coupled to a thread formed on an outer circumferential surface of the screw shaft 112a, and the insert protrusion 112c formed on an end portion of the length adjustment rod 112b exposed from the hand piece 100 and 101.

The screw shaft 112a may have the thread formed on the outer circumferential surface thereof along the lengthwise direction, and a screw nut 110a may be threaded onto the screw shaft 112a. In this case, the screw shaft 112a may have a male thread formed, and the screw nut 110a may have a female thread formed. The screw nut 110a may be integrally coupled to the length adjustment rod 112b. Thereby, when the screw nut 110a is moved by rotation of the screw shaft 112a, the length adjustment rod 112b may be moved in the horizontal direction.

Accordingly, when the screw shaft 112a rotates in one rotational direction, the length adjustment rod 112b moves along a direction away from the screw shaft 112a, that is, the horizontal direction, and when the screw shaft 112a rotates in an opposite rotational direction, the length adjustment rod 112b moves in a direction toward the screw shaft 112a.

Here, the rotation and moving directions of the screw shaft 112a and the length adjustment rod 112b may be determined depending on whether the thread formed on the screw shaft 112a is a right-handed thread or a left-handed thread.

The insert protrusion 112c may be formed on an end portion opposite to an end portion of the length adjustment rod 112b to which the screw shaft 112a is coupled. The insert protrusion 112c may be disposed in a position where the insert protrusion 112c is inserted into the insert recess 421 to be described below, that is, may be disposed to be coaxial with the insert recess 421.

The auxiliary shaft 111 disposed parallel to the main shaft 112 may be provided inside the cartridge housing 200.

Figure 6:
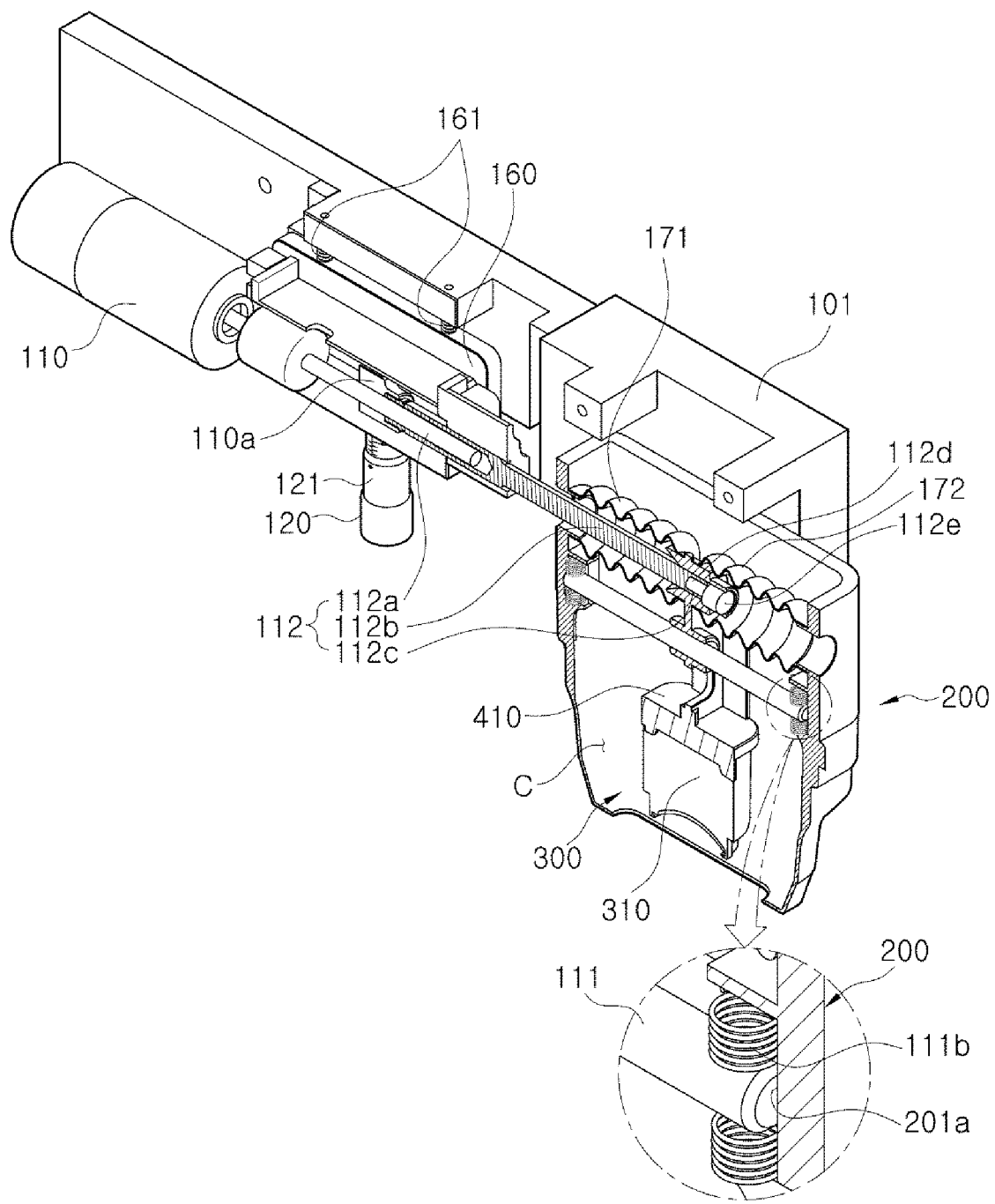
FIG. 6 is a perspective view of FIG. 5.

FIG. 6 is a perspective view of FIG. 5. As illustrated in FIG. 6, the insert protrusion 112c of the main shaft 112 may completely pass through an inner space of a first tube 171 in the lengthwise direction, and one portion of the main shaft 112 may be located inside a second tube 172. This state may be defined as an initial position.

The first tube 171 and the second tube 172 may be corrugated tubes that are deformable in the lengthwise direction.

Opposite end portions of the auxiliary shaft 111 may be elastically supported by second elastic members 111b in a process in which the auxiliary shaft 111 performs reciprocating motion in the vertical direction.

Guide recesses 201a may be formed on inside walls of the cartridge housing 200. The guide recesses 201a may provide spaces in which the opposite end portions of the auxiliary shaft 111 move in the vertical direction, and the second elastic members 111b may be located at upper ends and lower ends of the guide recesses 201a.

The guide member 400 may be coupled to the auxiliary shaft 111 so as to slide along an outer circumferential surface of the auxiliary shaft 111.

The guide member 400 may include a lower mount 410 protruding such that the ultrasound generation portion 300 having the transducer 310 as will be described below is mounted on one side of the guide member 400 and an upper mount 420 that protrudes from the guide member 400 to an other side and that is coupled to surround an outer circumferential surface of the main shaft 112.

The lower mount 410 protrudes toward a light transmitting window 320 of the cartridge housing 200, and the ultrasound generation portion 300 is mounted on the lower mount 410. Accordingly, ultrasound generated from the ultrasound generation portion 300 is emitted through the light transmitting window 320.

The ultrasound generation portion 300 may be electrically connected to an RF board (not illustrated) by a cable connector (not illustrated) of the hand piece 100 and 101. The ultrasound generation portion 300 may receive an electrical signal from the RF board and may cause the transducer 310 to emit focused ultrasound. As a result, the ultrasound emitted by the transducer 310 may be focused on a specific position. The specific position on which the ultrasound emitted by the transducer 310 is focused may be defined as a focus.

In addition, the distance from a tip end of the cartridge housing 200 to the focus may be determined as the ultrasonic focusing depth of the ultrasound generation portion 300. In this embodiment, the ultrasonic focusing depth of the ultrasound generation portion 300 may be adjusted depending on a movement of the ultrasound generation portion 300 in the vertical direction. A description thereabout will be given below.

Due to the nature of ultrasound, a liquid medium may be required. In particular, to minimize a loss of ultrasound, a medium having a low loss factor, for example, degassed liquid from which gas is removed may be received inside the cartridge housing 200.

When the main shaft 112 moves in the vertical direction, the upper mount 420 may cause the auxiliary shaft 111 to move in the vertical direction in conjunction with the movement of the main shaft 112.

The upper mount 420 may include the insert recess 421 into which the insert protrusion 112c is inserted. A first magnetic member 112d having an S or N polarity may be provided in the insert protrusion 112c, and a second magnetic member 112e having a polarity opposite to the polarity of the first magnetic member 112d may be provided in the insert recess 421 to correspond to the first magnetic member 112d.

When the insert protrusion 112c is inserted into the insert recess 421, an attractive force may act between the first magnetic member 112d and the second magnetic member 112e, and when the main shaft 112 moves in the horizontal direction as will be described below, the guide member 400 may be moved along the outer circumferential surface of the auxiliary shaft 111 by the attractive force. In this case, the auxiliary shaft 111 performs a function of guiding a stable movement of the main shaft 112 in the horizontal direction.

An inclined guide surface 422 having an inner diameter greater than the diameter of the insert protrusion 112c may be formed at an inlet side of the insert recess 421 through which the insert protrusion 112c is inserted into the insert recess 421, and the inner diameter of the inclined guide surface 422 may be gradually decreased and may be formed to converge to the diameter of the insert protrusion 112c. As the position of the upper mount 420 right before insertion of the insert protrusion 112c into the insert recess 421 is variable depending on the position of the auxiliary shaft 111, the inclined guide surface 422 may correct a position where the insert protrusion 112c and the insert recess 421 are coupled to each other, until the insert protrusion 112c and the insert recess 421 are disposed on the same axis.

In other words, even though the axis of the insert protrusion 112c is misaligned with the axis of the insert recess 421 by a predetermined distance, the insert protrusion 112c generates friction with the inclined guide surface 422 while being moved toward the insert recess 421, and the inclined guide surface 422 makes a correction such that the axis of the insert protrusion 112c and the axis of the insert recess 421 are smoothly aligned with each other.

The first tube 171 may be disposed to surround the length adjustment rod 112b. One end of the first tube 171 in the lengthwise direction may be supported on an inside wall of the cartridge housing 200, and an other end of the first tube 171 may be pressed against the upper mount 420. A sealing member (not illustrated) may be additionally provided on a contact surface where the first tube 171 is pressed against the upper mount 420. The sealing member ensures air-tightness such that the degassed liquid does not infiltrate into the first tube 171.

The second tube 172 may be disposed to be coaxial with the first tube 171 with respect to the upper mount 420. One end of the second tube 172 in the lengthwise direction may be pressed against the upper mount 420, and an other end of the second tube 172 may be supported on an inside wall of the cartridge housing 200. As in the case of the first tube 171, another sealing member (not illustrated) may be additionally provided on a contact surface between the second tube 172 and the upper mount 420. The other sealing member ensures air-tightness such that the degassed liquid does not infiltrate into the second tube 172.

In addition, the first tube 171 and the second tube 172 may have an oval cross-sectional shape in which the length in the vertical direction is greater than the lengths in the other directions. As the first tube 171 and the second tube 172 are formed in an oval cross-sectional shape, a moving range of the main shaft 112 may be ensured in a process in which the main shaft 112 moves in the vertical direction, and air-tightness between the inside and the outside of the cartridge housing 200 may be ensured.

Furthermore, the first tube 171 and the second tube 172 may be formed of a soft material such as urethane, silicone, or the like. Accordingly, air-tightness reliability may be ensured by preventing leakage of the medium by suppressing occurrence of a gap between the first tube 171 and the upper mount 420 or between the second tube 172 and the upper mount 420.

Hereinafter, an operational process of the ultrasonic generator with the adjustable ultrasonic focusing depth according to an embodiment of the inventive concept will be described.

Referring again to FIGS. 4 and 5, when a user mounts the cartridge housing 200 in the mounting frame 101, the ultrasonic generator is in the state of FIG. 4, and when the user initially drives the first actuator 110 (for example, when the user causes the first actuator 110 to make one revolution), the length adjustment rod 112b of the main shaft 112 is moved toward the upper mount 420 in the horizontal direction as illustrated in FIG. 5.

Even though the axis of the insert protrusion 112c of the length adjustment rod 112b is misaligned with the axis of the insert recess 421 by a predetermined distance, the insert protrusion 112c may be inserted into the insert recess 421 while generating friction with the inclined guide surface 422. In this process, a coupling of the insert protrusion 112c and the insert recess 421 may be smoothly performed by an attractive force between the first magnetic member 112d provided in the insert protrusion 112c and the second magnetic member 112e provided in the insert recess 421.

Figure 7:
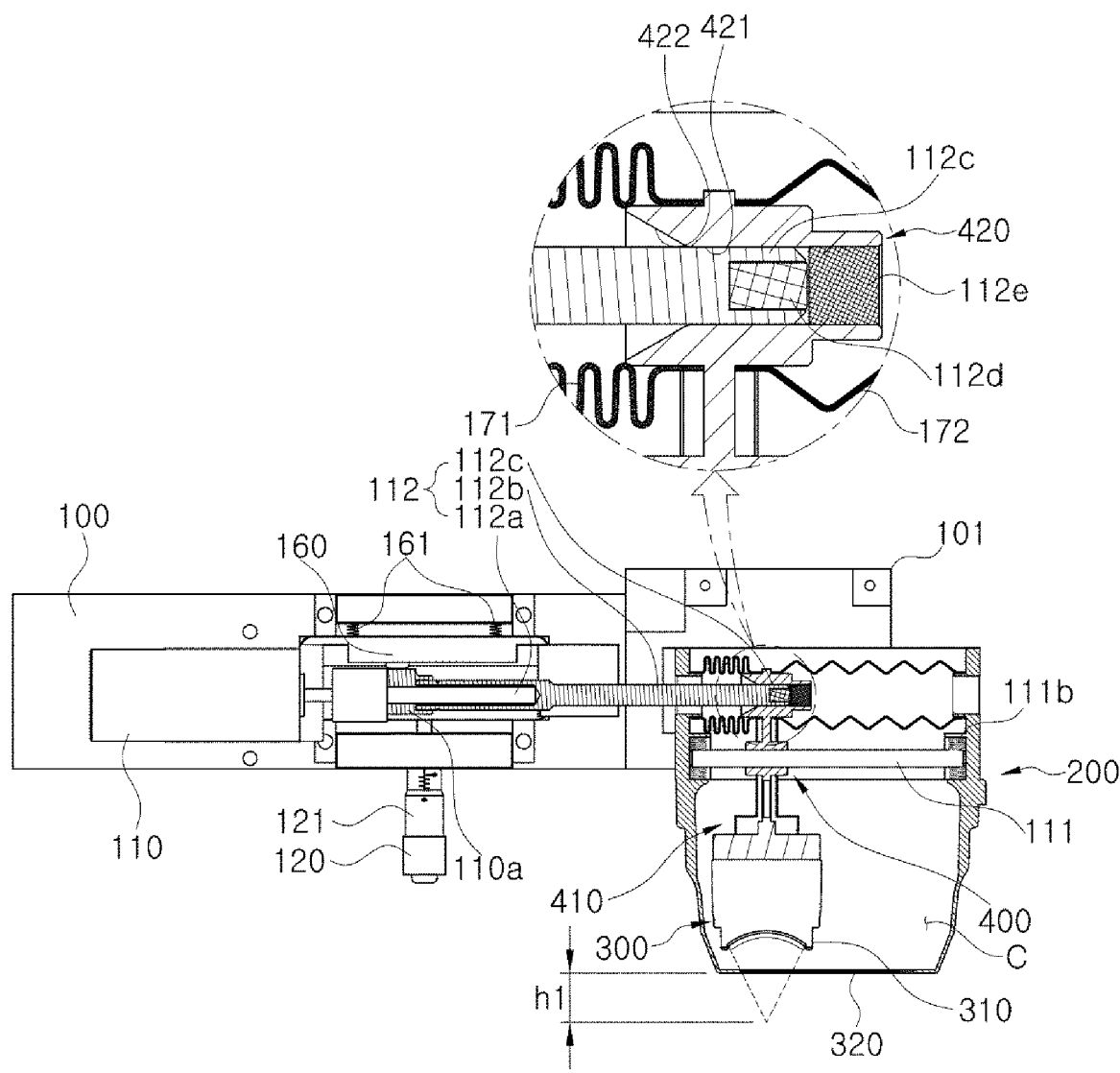
FIG. 7 is a view illustrating a state in which an ultrasound generation portion is moved to the left in a horizontal direction in the state of FIG. 5.

FIG. 7 is a view illustrating a state in which the ultrasound generation portion is moved to the left in the horizontal direction in the state of FIG. 5.

Referring to FIG. 7, the ultrasound generation portion 300 having the transducer 310 may be moved to the left in the horizontal direction while maintaining an ultrasonic focusing depth h1. The ultrasound generation portion 300 may be moved to the left as the length adjustment rod 112b moves leftward depending on a movement of the screw nut 110a, which is screw-coupled to the screw shaft 112a, in a process in which the screw shaft 112a rotates when the first actuator 110 rotates in one rotational direction. Thereby, the focus of ultrasound emitted from the transducer 310 may be moved to the left. Accordingly, a procedure may be more rapidly performed on a wide portion in an easy and simple manner.

Furthermore, considering a range that covers various treatment areas, the ultrasound generation portion 300 may be moved within the range from 0.1 mm to 50 mm, preferably from 0.1 mm to 30 mm depending on design values of the numbers or pitches of the threads of the screw shaft 112a and the screw nut 110a.

Figure 8:
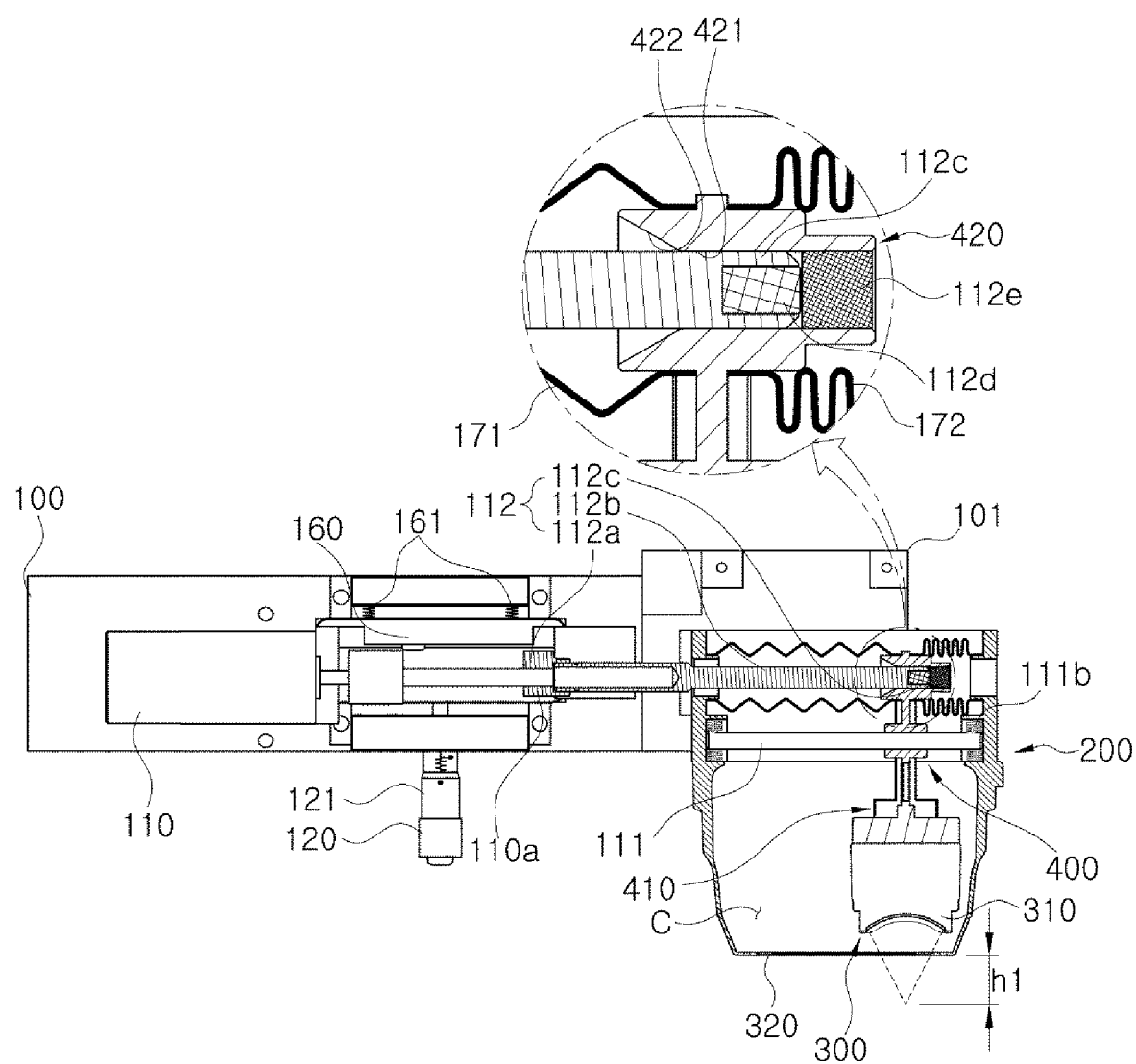
FIG. 8 is a view illustrating a state in which the ultrasound generation portion is moved to the right in the horizontal direction in the state of FIG. 5.

FIG. 8 is a view illustrating a state in which the ultrasound generation portion 300 is moved to the right in the horizontal direction in the state of FIG. 5.

Referring to FIG. 8, the ultrasound generation portion 300 having the transducer 310 may be moved to the right in the horizontal direction while maintaining the ultrasonic focusing depth h1. The ultrasound generation portion 300 may be moved to the right as the length adjustment rod 112b moves rightward depending on a movement of the screw nut 110a, which is screw-coupled to the screw shaft 112a, in a process in which the screw shaft 112a rotates when the first actuator 110 rotates in an opposite rotational direction. Thereby, the focus of ultrasound emitted from the transducer 310 may be moved to the right. Accordingly, a procedure may be more rapidly performed on a wide portion in an easy and simple manner.

Figure 9:
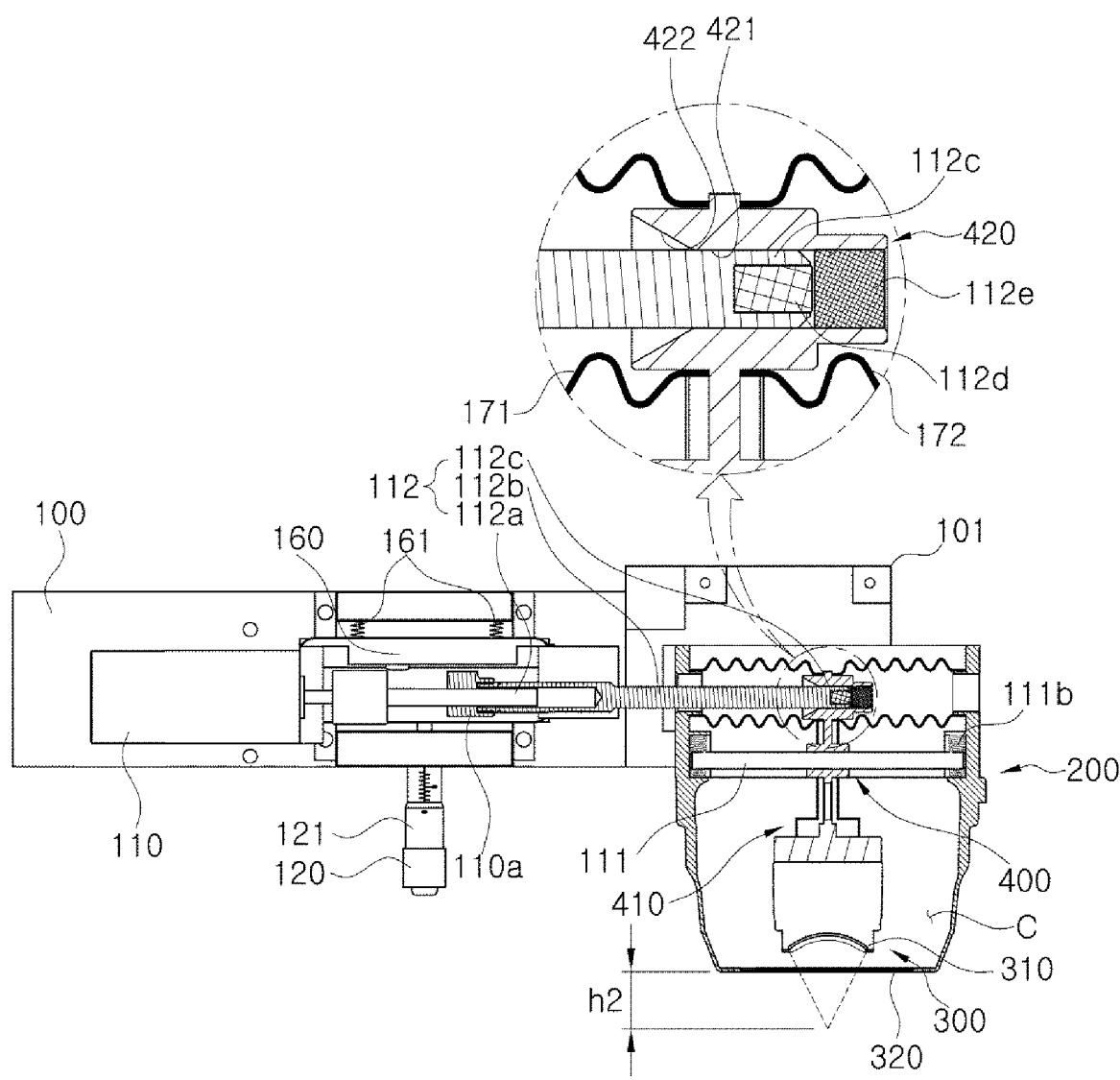
FIG. 9 is a view illustrating a state in which the ultrasound generation portion is moved downward along a vertical direction in the state of FIG. 5.

FIG. 9 is a view illustrating a state in which the ultrasound generation portion 300 is moved downward in the vertical direction in the state of FIG. 5.

Referring to FIG. 9 together with FIG. 5, in the state of FIG. 5, the ultrasonic focusing depth is in a state of h1, whereas in the state of FIG. 9, the ultrasonic focusing depth is in a state of h2 because the ultrasound generation portion 300 is moved downward in the vertical direction.

In other words, the ultrasonic focusing depth h2 refers to a value greater than the ultrasonic focusing depth h1, and as the ultrasonic focusing depth is changed from h1 to h2, the state of FIG. 9 may be used in a case where a fat layer thickness or abdominal circumference of a person under a procedure is large. Here, the ultrasonic focusing depth of the ultrasound generation portion 300 in the vertical direction may be, for example, designed to be moved to a depth of 0.1 mm to 5 mm.

The ultrasound generation portion 300 may be moved downward by operation of the outer rotor 120 and the inner rotor 121.

Specifically, the length by which the inner rotor 121 protrudes from the outer rotor 120 is decreased by rotation of the outer rotor 120. Here, the outer rotor 120 may be manually rotated by a user, or may be automatically rotated by a drive means such as a drive motor.

As a result, with the decrease in the length by which the inner rotor 121 protrudes from the outer rotor 120, the first elastic members 161 are extended to press the movable plate 160 downward.

At this time, the ultrasound generation portion 300 may be moved downward as the main shaft 112 fixed to the movable plate 160, the first actuator 110, the auxiliary shaft 111, the ultrasound generation portion 300, and the guide member 400 are moved downward together.

When the ultrasound generation portion 300 is moved downward, the ultrasonic focusing depth of the ultrasound generation portion 300 is increased.

Figure 10:
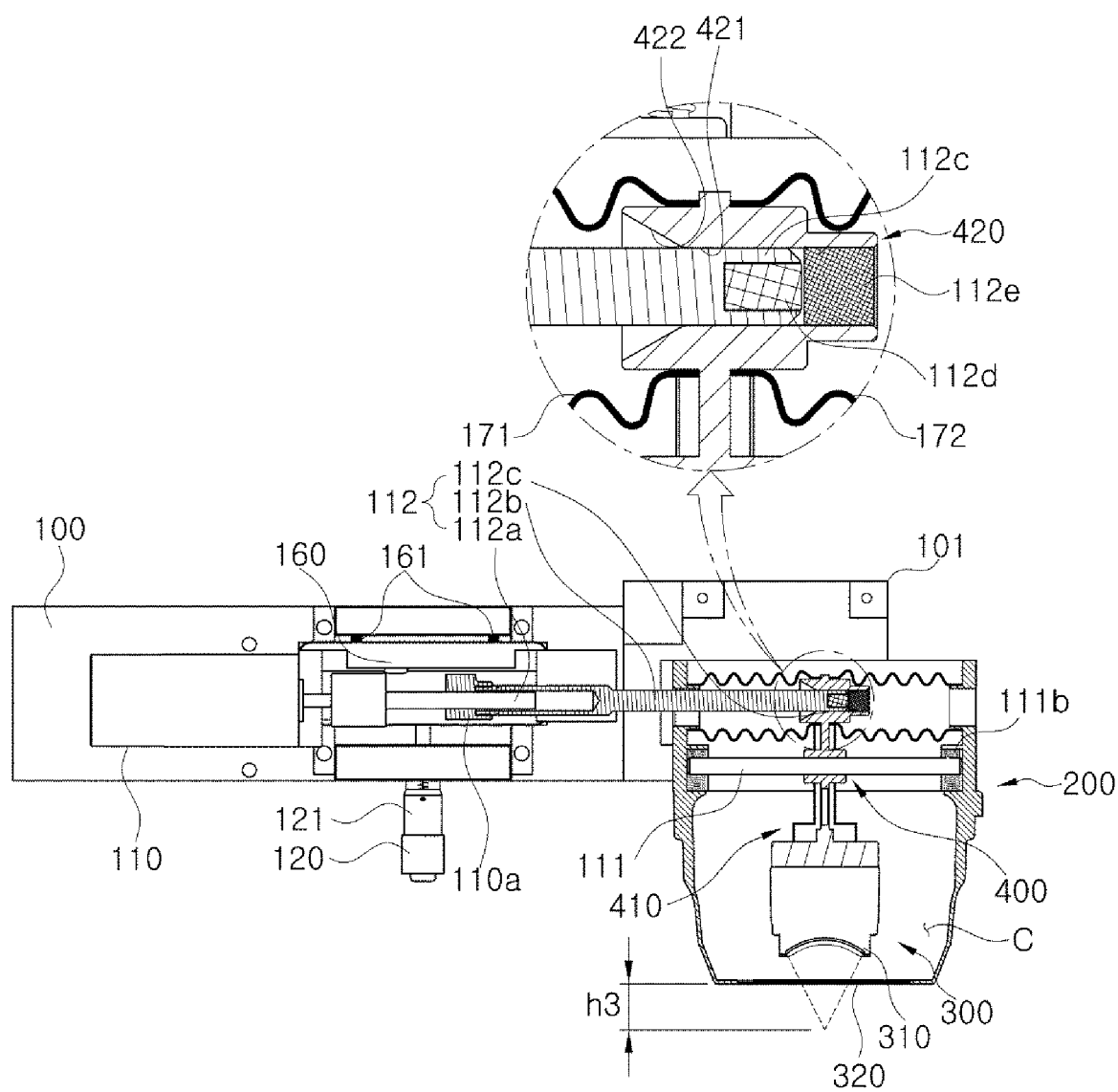
FIG. 10 is a view illustrating a state in which the ultrasound generation portion is moved upward in the vertical direction in the state of FIG. 5.

FIG. 10 is a view illustrating a state in which the ultrasound generation portion is moved upward in the vertical direction in the state of FIG. 5.

Referring to FIG. 10 together with FIG. 5, in the state of FIG. 5, the ultrasonic focusing depth is in a state of h1, whereas in the state of FIG. 10, the ultrasonic focusing depth is in a state of h3 because the ultrasound generation portion 300 is moved upward in the vertical direction.

In other words, the ultrasonic focusing depth h3 refers to a value smaller than the ultrasonic focusing depth h1, and as the ultrasonic focusing depth is changed from h1 to h3, the state of FIG. 10 may be used in a case where a fat layer thickness or abdominal circumference of a person under a procedure is small.

The ultrasound generation portion 300 may be moved upward by operation of the outer rotor 120 and the inner rotor 121.

Specifically, the length by which the inner rotor 121 protrudes from the outer rotor 120 is increased by rotation of the outer rotor 120. Here, the outer rotor 120 may be manually rotated by a user, or may be automatically rotated by a drive means such as a drive motor.

As a result, with the increase in the length by which the inner rotor 121 protrudes from the outer rotor 120, the first elastic members 161 are compressed, and the movable plate 160 is moved upward.

At this time, the ultrasound generation portion 300 may be moved down ward as the main shaft 112 fixed to the movable plate 160, the first actuator 110, the auxiliary shaft 111, the ultrasound generation portion 300, and the guide member 400 are moved upward together.

When the ultrasound generation portion 300 is moved upward, the ultrasonic focusing depth of the ultrasound generation portion 300 is decreased.

As described above, the ultrasound generation portion 300 may be disposed so as to be movable in the horizontal direction and the vertical direction. During a procedure, the ultrasound generation portion 300 may be alternately moved in the horizontal direction and the vertical direction to aim for an accurate ultrasonic focusing depth for a treatment area.

According to this embodiment, it is possible to minimize the inconvenience of needing to purchase cartridges having corresponding ultrasonic focusing depths, or replace a provided cartridge, depending on various fat layer thicknesses or abdominal circumferences of persons under procedures.

Figure 11:
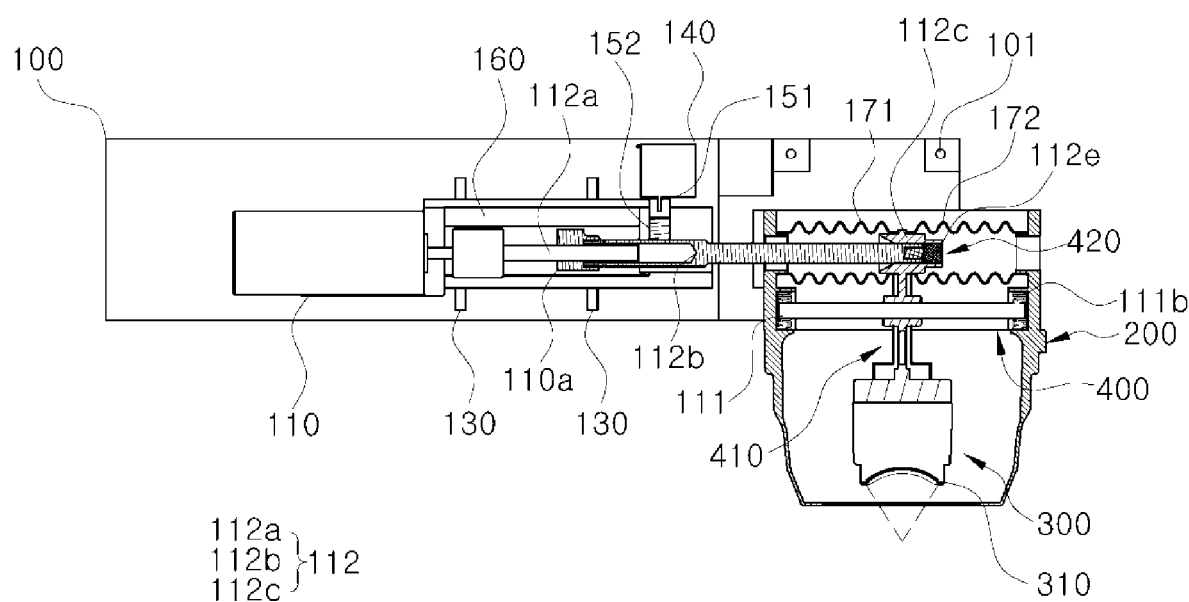
FIG. 11 is a schematic view illustrating an ultrasonic generator with an adjustable ultrasonic focusing depth according to another embodiment of the inventive concept.
Figure 12:
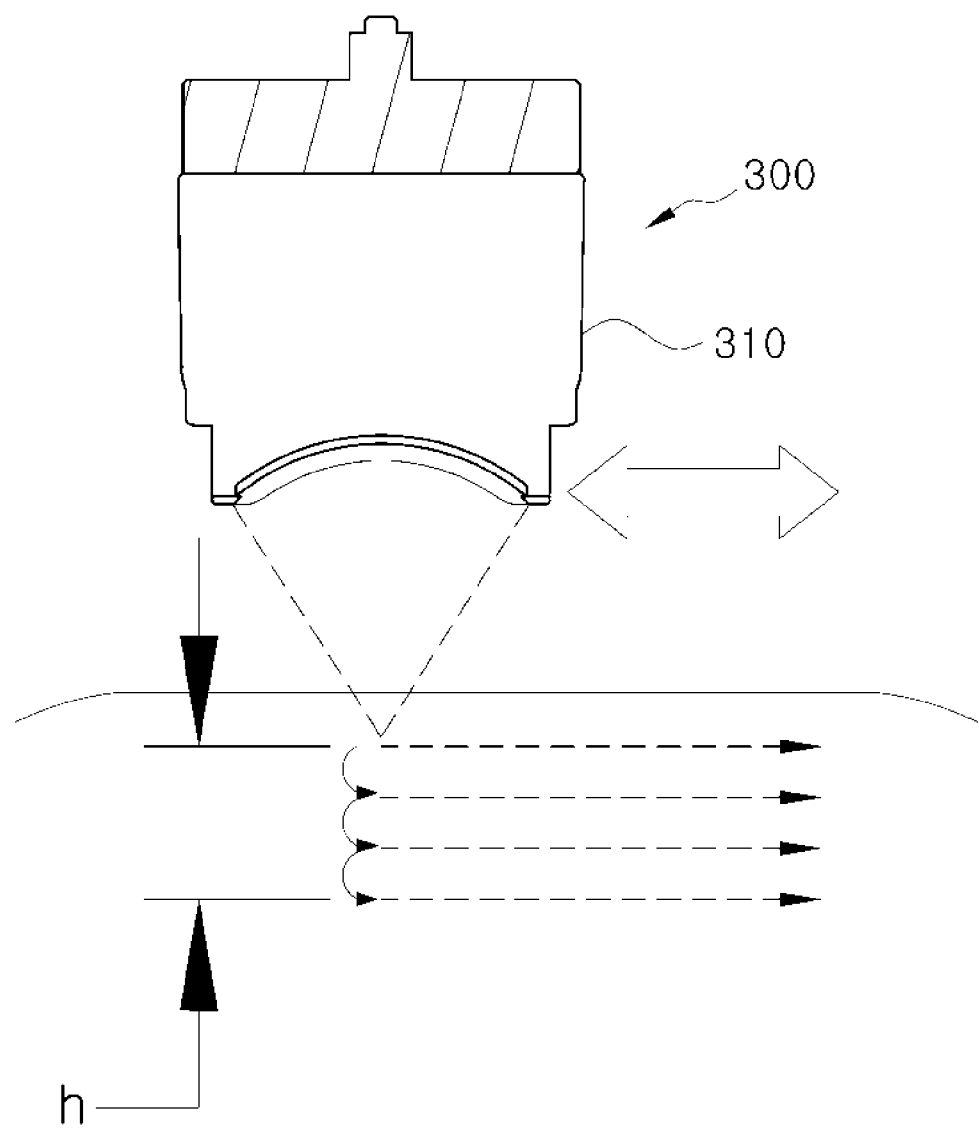
FIGS. 12 and 13 are schematic views illustrating methods for treating obesity by altering a focal distance in the horizontal and vertical directions using the ultrasonic generator with the adjustable ultrasonic focusing depth according to another embodiment of the inventive concept.
Figure 13:
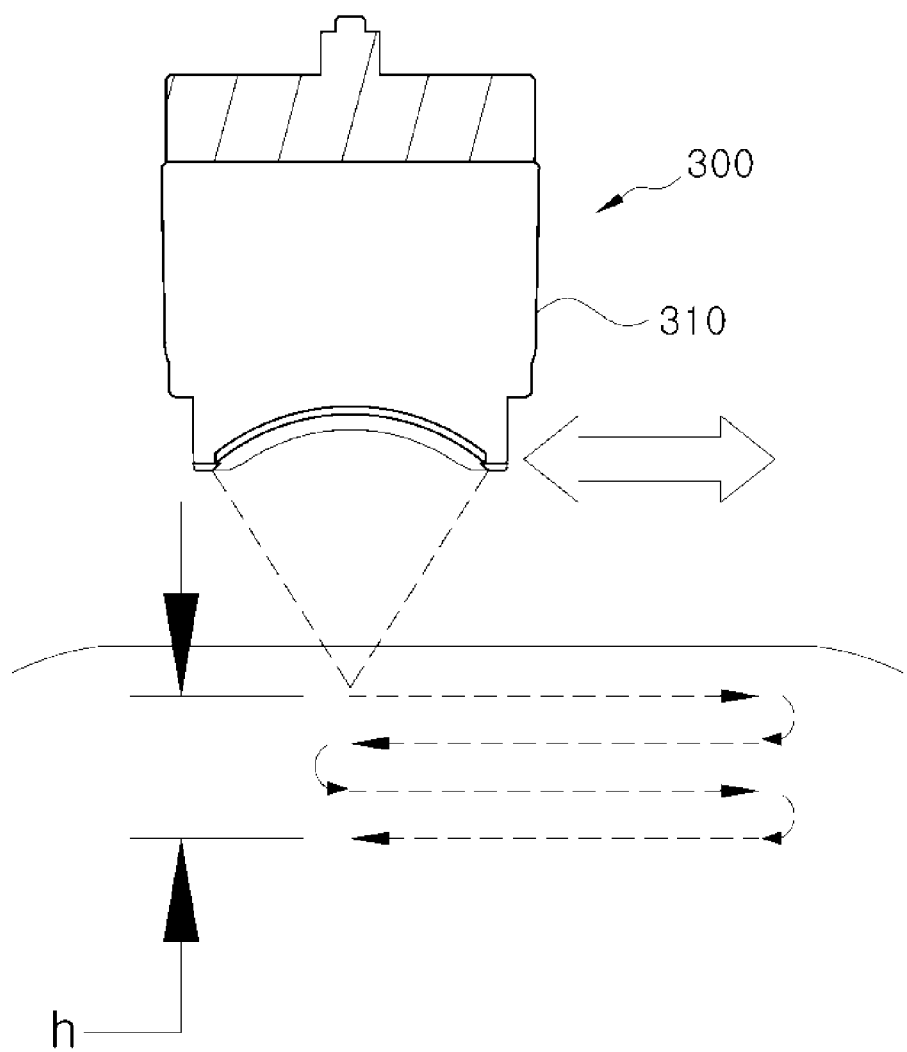

FIG. 11 is a schematic view illustrating an ultrasonic generator with an adjustable ultrasonic focusing depth according to another embodiment of the inventive concept. FIGS. 12 and 13 are schematic views illustrating methods for treating obesity by altering a focal distance in the horizontal and vertical directions using the ultrasonic generator with the adjustable ultrasonic focusing depth according to the other embodiment of the inventive concept.

As illustrated in FIG. 11, in order to automatically move an ultrasound generation portion 300 along a vertical direction, the ultrasonic generator with the adjustable ultrasonic focusing depth according to another embodiment of the inventive concept may further include guides 130 and a second actuator 140.

The guides 130 are provided between a hand piece 100 and 101 and a movable plate 160 in the vertical direction and are coupled to the hand piece 100 and 101. The movable plate 160 may be coupled so as to be movable along the guides 130, or may be moved in the vertical direction by itself. The second actuator 140 moves the movable plate 160 in the vertical direction. A first actuator 110, an auxiliary shaft 111, a main shaft 112, a length adjustment rod 112b, the ultrasound generation portion 300, and a guide member 400 may be moved together in the vertical direction in conjunction with the vertical movement of the movable plate 160. Accordingly, the ultrasonic focusing depth of the ultrasound generation portion 300 may be adjusted. At this time, the movable plate 160 may be linearly moved along the guides 130, or may be moved in the vertical direction by itself.

For example, the second actuator 140 may be a drive motor that moves the movable plate 160 in the vertical direction. A screw shaft 151 may be coupled to a drive shaft of the drive motor of the second actuator 140, and a screw nut 152 screw-coupled to the screw shaft 151 may be provided on the movable plate 160.

Accordingly, when the screw shaft 151 is rotated by the second actuator 140, the screw nut 152 and the movable plate 160 may be moved in the vertical direction along the screw shaft 151. The first actuator 110, the auxiliary shaft 111, the main shaft 112, the length adjustment rod 112b, the ultrasound generation portion 300, and the guide member 400 may be moved together in the vertical direction in conjunction with the vertical movement of the screw nut 152 and the movable plate 160. Accordingly, the ultrasonic focusing depth of the ultrasound generation portion 300 may be adjusted. At this time, the movable plate 160 may be linearly moved along the guides 130, or may be moved in the vertical direction by itself.

As described above, a screw nut 110a may be moved in a horizontal direction along a screw shaft 112a when the screw shaft 112a is rotated by rotation of a drive motor of the first actuator 110.

The length adjustment rod 112b, an insert protrusion 112c, the ultrasound generation portion 300, and the guide member 400 may be moved together in the horizontal direction in conjunction with the horizontal movement of the screw nut 110a. Accordingly, the focus of ultrasound of the ultrasound generation portion 300 may be moved in the horizontal direction. At this time, the second actuator 140 may be fixed to the hand piece 100 and 101.

As a result, in this embodiment, the ultrasound generation portion 300 may be moved in the horizontal direction by the first actuator 110. At this time, the focus of ultrasound of the ultrasound generation portion 300 may be moved in the horizontal direction in a deep portion of the skin.

Furthermore, in this embodiment, the ultrasound generation portion 300 may be moved in the vertical direction by the second actuator 140. At this time, the focus of ultrasound of the ultrasound generation portion 300 may be moved in the vertical direction in the deep portion of the skin. The movement of the focus may correspond to a change of the ultrasonic focusing depth of the ultrasound generation portion 300.

The ultrasonic generator with the adjustable ultrasonic focusing depth according to another embodiment of the inventive concept may automatically adjust the position of the ultrasound generation portion 300, based on a user interface having a display (not illustrated) that displays distances by which the focus of ultrasound of the ultrasound generation portion 300 is moved in the deep portion of the skin in the horizontal direction and the vertical direction.

The display may be provided on an ultrasonic generator body (not illustrated), the hand piece 100 and 101, or a cartridge housing 200, and a user interface for inputting target values for the distances by which the focus of ultrasound of the ultrasound generation portion 300 is moved in the deep portion of the skin in the horizontal direction and the vertical direction is displayed on a screen of the display.

For example, the display may be implemented with a touch pad, and the user interface may be implemented with a keypad for inputting the target values for the distances by which the focus of ultrasound of the ultrasound generation portion 300 is moved in the deep portion of the skin in the horizontal direction and the vertical direction.

In another example, the display may be implemented with a touch pad, and the user interface may be implemented with a plurality of icons on which the target values for the distances by which the focus of ultrasound of the ultrasound generation portion 300 is moved in the deep portion of the skin in the horizontal direction and the vertical direction are displayed.

The ultrasonic generator with the adjustable ultrasonic focusing depth according to another embodiment of the inventive concept may automatically adjust the vertical position and the horizontal position of the ultrasound generation portion 300, based on a switch located on the hand piece.

Hereinafter, methods of treating obesity by altering moving distances in the horizontal and vertical directions using the ultrasonic generator with the adjustable ultrasonic focusing depth according to another embodiment of the inventive concept will be described.

A user inputs, to the user interface, distances by which the focus of ultrasound of the ultrasound generation portion 300 is moved in a deep portion of the skin in the horizontal and vertical directions.

The user interface may alternately or irregularly operate the first actuator 110 and the second actuator 140 depending on the input distances by which the focus of ultrasound of the ultrasound generation portion 300 is moved in the deep portion of the skin in the horizontal and vertical directions. Movements of the ultrasound generation portion 300 in the horizontal and vertical directions may be alternately performed by the alternate operations of the first actuator 110 and the second actuator 140.

For example, as illustrated in FIG. 12, a process of moving the ultrasound generation portion 300 in a forward horizontal direction, that is, to the right by the first actuator 110, a process of moving the ultrasound generation portion 300 in a reverse horizontal direction, that is, to the left by the first actuator 110, and a process of moving the ultrasound generation portion 300 in the vertical direction by the second actuator 140 may be repeated in one cycle.

Furthermore, as illustrated in FIG. 13, a process of moving the ultrasound generation portion 300 in the forward horizontal direction, that is, to the right by the first actuator 110, a process of moving the ultrasound generation portion 300 in the vertical direction by the second actuator 140, a process of moving the ultrasound generation portion 300 in the reverse horizontal direction, that is, to the left by the first actuator 110, and a process of moving the ultrasound generation portion 300 in the vertical direction by the second actuator 140 may be repeated in one cycle.

As the ultrasound generation portion 300 is moved in the horizontal and vertical directions, the focus of ultrasound of the ultrasound generation portion 300 in the deep portion of the skin is moved in the horizontal and vertical directions.

Accordingly, in the methods of treating obesity by altering the moving distances in the horizontal and vertical directions using the ultrasonic generator with the adjustable ultrasonic focusing depth according to another embodiment of the inventive concept, the focus of ultrasound of the ultrasound generation portion 300 in the deep portion of the skin may be automatically moved in the horizontal and vertical directions by the first actuator 110 and the second actuator 140. Accordingly, area treatment may be performed in the deep portion of the skin, and a relatively wide portion may be treated at one time in the deep portion of the skin.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

The invention claimed is:

1. An ultrasonic generator with an adjustable ultrasonic focusing depth, the ultrasonic generator comprising:
a cartridge housing in which an ultrasound generation portion configured to generate ultrasound is provided;
a hand piece in which the cartridge housing is detachably mounted, the hand piece having a first actuator thereinside;
a main shaft to which the ultrasound generation portion is coupled to move the ultrasound generation portion in a horizontal direction, parallel to the bottom of the cartridge housing and a vertical direction, perpendicular to the bottom of the cartridge housing,
wherein one end of the main shaft is coupled to one end of the first actuator of the hand other another end of the main shaft is located inside the cartridge housing, and piece, and
wherein the hand piece includes an adjustment portion configured to adjust an ultrasonic focusing depth of the ultrasound generation portion by adjusting an amount of movement of the main shaft in the vertical direction;
an auxiliary shaft accommodated in the cartridge housing, disposed parallel to the main shaft, and configured to guide a movement of the ultrasound generation portion in the vertical direction and the horizontal direction;
second elastic members configured to elastically support movement of the auxiliary shaft in the vertical direction, wherein the second elastic members comprise:
a first-second elastic member positioned above a first end portion of the auxiliary shaft;
a second-second elastic member positioned below the first end portion of the auxiliary shaft;
a third-second elastic member positioned above a second end portion of the auxiliary shaft; and
a fourth-second elastic member positioned below the second end portion of the auxiliary shaft;
a first guide recess that is positioned on a first inside wall of the cartridge housing and provides a first space in which the first end portion of the auxiliary shaft moves in the vertical direction; and
a second guide recess that is positioned on a second inside wall of the cartridge housing and provides a second space in which the second end portion of the auxiliary shaft moves in the vertical direction;
wherein the first-second elastic member is located in an upper end of the first guide recess, the second-second elastic member is located in an lower end of the first guide recess the third-second elastic member is located in an upper end of the second guide recess and the fourth-second elastic member is located in an lower end of the second guide recess.

2. The ultrasonic generator of claim 1, further comprising:
a movable plate to which the main shaft is fixed, the movable plate being provided so as to be movable inside the hand piece in the vertical direction.

3. The ultrasonic generator of claim 2, wherein the adjustment portion is located to press one side surface of the movable plate for movement of the ultrasound generation portion in the vertical direction, and
wherein the ultrasonic generator further comprises a first elastic member disposed on an opposite side to the adjustment portion in the vertical direction with the movable plate therebetween and configured to elastically support an opposite side surface of the movable plate.

4. The ultrasonic generator of claim 1, further comprising:
a guide member configured to slide along an outer circumferential surface of the auxiliary shaft;
wherein the ultrasound generation portion is fixed to a lower mount protruding from the guide member to one side, and an upper mount protruding from the guide member to another side is coupled to the main shaft.

5. The ultrasonic generator of claim 4, wherein the main shaft includes:
a screw shaft directly connected to the first actuator and configured to integrally rotate together with the first actuator;
a screw nut screw-coupled to a thread formed on an outer circumferential surface of the screw shaft and configured to move in the horizontal direction when the screw shaft rotates;
a length adjustment rod integrally coupled to the screw nut and configured to move together with the screw nut; and
an insert protrusion formed on an end portion of the length adjustment rod exposed from the hand piece, the insert protrusion being detachably coupled to the upper mount.

6. The ultrasonic generator of claim 5, wherein the upper mount includes an insert recess into which the insert protrusion is inserted, and a first tube and a second tube are disposed at both ends of the insert recess in the horizontal direction.

7. The ultrasonic generator of claim 6, wherein the insert protrusion includes a magnetic member having a polarity, and the insert recess includes a magnetic member having a polarity opposite to the polarity of the magnetic member of the insert protrusion.

8. The ultrasonic generator of claim 6, wherein an inclined guide surface having an inner diameter greater than a diameter of the insert protrusion is formed at an inlet side of the insert recess, and the inner diameter of the inclined guide surface is formed to converge to the diameter of the insert protrusion.

9. The ultrasonic generator of claim 6, wherein the first tube is spaced apart from an outer circumferential surface of the length adjustment rod so as to surround the length adjustment rod and has one end supported on an inside wall of the cartridge housing in the horizontal direction and another end pressed against the upper mount.

10. The ultrasonic generator of claim 9, wherein the upper mount is disposed between the first tube and the second tube, and wherein the second tube has one end pressed against the upper mount and another end supported on an inside wall of the cartridge housing.

11. The ultrasonic generator of claim 10, wherein the upper mount further includes a fixing member formed such that portions of outer circumferential surfaces of the first and second tubes are simultaneously stopped by and fixed to the fixing member between the first tube and the second tube.

12. The ultrasonic generator of claim 2, further comprising:
a second actuator configured to move the movable plate in the vertical direction, wherein a screw shaft is coupled to the second actuator, and wherein a screw nut screw-coupled to the screw shaft is provided on the movable plate.

* * * * *

UNITED STATES PATENT AND TRADEMARK OFFICE
CERTIFICATE OF CORRECTION

| | | |
|---|---|---|
| PATENT NO. | : 12,097,391 B2 | Page 1 of 1 |
| APPLICATION NO. | : 17/344321 | |
| DATED | : September 24, 2024 | |
| INVENTOR(S) | : Eun Ho Kim et al. | |

It is certified that error appears in the above-identified patent and that said Letters Patent is hereby corrected as shown below:

In the Claims

Claim 1: Column 15, Line 18: "of the first actuator of the hand other another end of the" should read -- of the first actuator of the hand piece, and another end of the --.

Claim 1: Column 15, Line 20: "piece, and" should be deleted.

Claim 1: Column 15, Lines 51-52: "guide recess the third-second elastic member is located in an upper end of the second guide recess and the" should read -- guide recess, the third-second elastic member is located in an upper end of the second guide recess, and the --.

Signed and Sealed this
Twelfth Day of August, 2025

Coke Morgan Stewart
*Acting Director of the United States Patent and Trademark Office*